US009770037B2

(12) United States Patent
Jenkins

(10) Patent No.: US 9,770,037 B2
(45) Date of Patent: *Sep. 26, 2017

(54) BIO-STIMULANT FOR IMPROVED PLANT GROWTH AND DEVELOPMENT

(71) Applicant: Donaghys Limited, Harewood (NZ)

(72) Inventor: Timothy Allen Jenkins, Christchurch (NZ)

(73) Assignee: DONAGHYS LIMITED, Harewood (NZ)

( * ) Notice: Subject to any disclaimer, the term of this patent is extended or adjusted under 35 U.S.C. 154(b) by 119 days.

This patent is subject to a terminal disclaimer.

(21) Appl. No.: 14/838,143

(22) Filed: Aug. 27, 2015

(65) Prior Publication Data

US 2016/0050938 A1 Feb. 25, 2016

Related U.S. Application Data

(63) Continuation of application No. 14/179,351, filed on Feb. 12, 2014, now Pat. No. 9,131,700, which is a continuation of application No. 13/256,717, filed as application No. PCT/NZ2009/000037 on Mar. 23, 2009, now Pat. No. 8,709,977.

(51) Int. Cl.
| *A01N 63/00* | (2006.01) |
| *A01N 63/02* | (2006.01) |
| *A01N 63/04* | (2006.01) |
| *C05C 9/00* | (2006.01) |
| *C12N 1/18* | (2006.01) |
| *C12N 1/20* | (2006.01) |
| *C12P 1/02* | (2006.01) |
| *C12P 1/04* | (2006.01) |
| *C05G 3/00* | (2006.01) |

(52) U.S. Cl.
CPC ............ *A01N 63/02* (2013.01); *A01N 63/04* (2013.01); *C05C 9/00* (2013.01); *C05G 3/00* (2013.01); *C12N 1/18* (2013.01); *C12N 1/20* (2013.01); *C12P 1/02* (2013.01); *C12P 1/04* (2013.01)

(58) Field of Classification Search
None
See application file for complete search history.

(56) References Cited

U.S. PATENT DOCUMENTS

| 8,709,977 | B2 | 4/2014 | Jenkins | |
| 9,131,700 | B2 * | 9/2015 | Jenkins | .......... A01N 63/02 |
| 2004/0050335 | A1 | 3/2004 | Muller et al. | |
| 2004/0228931 | A1 | 11/2004 | Chokshi et al. | |

FOREIGN PATENT DOCUMENTS

| CN | 1470600 A | 1/2004 |
| CN | 1544610 A | 11/2004 |
| CN | 1966663 A | 5/2007 |
| JP | 06070782 | 3/1994 |
| JP | 09084520 | 3/1997 |
| JP | 2003189824 A | 7/2003 |
| KP | 2004108395 | 12/2004 |
| KP | 20080032809 | 4/2008 |
| RO | 87033 A2 | 5/1985 |
| WO | WO-0183400 A2 | 11/2001 |

OTHER PUBLICATIONS

Derwent DWPI Online Abstract Accession No. 2007-405294[39], CN 1900027 A (Yan Jianhua) Jan. 24, 2007.
Derwent DWPI Online Abstract Accession No. 2007-832003[78], CN 1966663 A (Li Ji) May 23, 2007.
Derwent DWPI Online Abstract Accession No. 2008-F24679[35], KR 20070112994 A (Gim Chin Yang) Nov. 28, 2007.
Derwent DWPI Online Abstract Accession No. 2009-A66791 [03], KR 20080032809 A (Republic of Korea Management Ministry) Apr. 16, 2008.
Kumar et al., Expression and secretion of a prokaryotic protein streptokinase without and glycosylation degradation Schizocaccharomyces pombe, Yeast, 2004, vol. 21 No. 16, p. 1343-58 (ABS).
Mishra et al., Structural and antimicrobial studies of compounds of VO(II), Co(II), Ni(II) and Cu(II) with some Schiff bases involving 2-amino-4-chlorophenol, Journal of the Serbian Chemistry Society, 2009, vol. 74, No. 5, pp. 523-525 (ABS).
Notification of Transmittal of International Preliminary Report on Patentability (Chapter II of the Patent Cooperation Treaty) re International Application No. PCT/NZ2009/000037, date of mailing Feb. 15, 2011.
Ottogalli et al., Microbiology of Pannerone cheese, Industria del Latte, 1975, vol. 11 No. 1, pp. 7-17 (Abs).
Ting et al., Bioremediation of petroleum-contaminated soil with a microbial mixture of yeast and bacteria, Research of Environmental Sciences, 2009, vol. 22, No. 12, pp. 1472-1477 (ABS).

* cited by examiner

Primary Examiner — Alton Pryor
(74) Attorney, Agent, or Firm — Perkins Coie LLP

(57) ABSTRACT

A bio-stimulant composition for obtaining improved plant growth, either combined or uncombined with urea and/or other agricultural compounds, as well of methods of producing and using said composition.

18 Claims, 1 Drawing Sheet

Graph of Pasture Dry Matter Production (kg/ha)
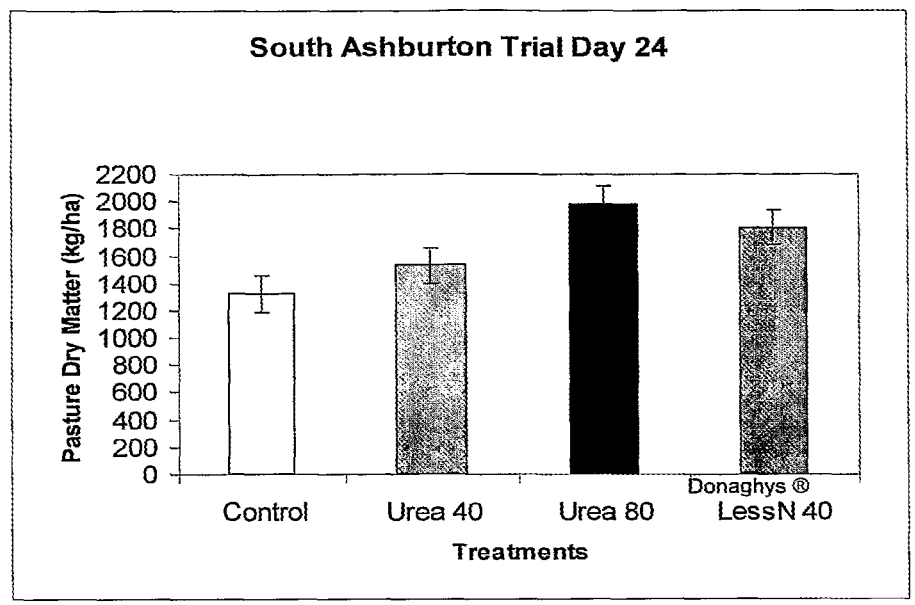

ent practices, including timing of application of fertiliser, split fertiliser applications, grazing management, pasture species choices, cropping type and landscape modification.

BIO-STIMULANT FOR IMPROVED PLANT GROWTH AND DEVELOPMENT

FIELD

Embodiments described herein encompass a method of improving plant growth responses, reducing nitrogen input, and improving plant development by application of a plant bio-stimulant composition in combination with urea and/or other agricultural compounds. A method for combining the composition with urea and/or other agricultural compounds is also encompassed. Embodiments described herein further encompass a bio-stimulant composition for obtaining improved plant growth, either combined or uncombined with urea and/or other agricultural compounds.

BACKGROUND

New Zealand has traditionally relied on clover and other legumes to biologically fix the nitrogen that is required to grow pasture. More recently, there has been increased use of nitrogen fertilisers such as urea to increase pasture production further and address seasonal deficits in feed supply.

There are a number of negative environmental consequences of excessive use of nitrogen fertilisers. The one that is most publicised is the potential to increase the level of nitrates that are leached into groundwater and can therefore pollute waterways. There are also implications relevant to the concern over greenhouse gases. The use of high amounts of nitrogen fertiliser can increase the level of denitrification that can occur leading to higher levels of nitrous oxide emissions (a potent greenhouse gas). Furthermore, the production of artificial nitrogen fertiliser is highly energy intensive; this energy requirement is derived from the burning of natural gas resulting in the production of the other greenhouse gas, carbon dioxide. This also represents a significant use of a limited natural gas resource increasingly important for other uses including electricity generation.

Use of nitrogen fertiliser is steadily increasing. In New Zealand, a country with an economy that relies heavily on dairy, sheep and beef farming, total fertiliser use increased by 113 percent from 1986 to 2002 (Statistics New Zealand, Fertiliser use and the environment, August 2006). The application of urea increased by approximately 27 percent between 2002 and 2004 (ibid.).

A problem with the application of nitrogen fertilisers is that often excess nitrogen is applied to the pasture. In addition, if nitrogen is not applied at the correct time, for example, if it is applied when plants are not actively growing, the loss of nitrogen is exacerbated. There are several approaches that have been taken to minimise adverse effects of fertiliser use. One such approach is the use of nitrification inhibitors.

The most common nitrification inhibitors are 2-chloro-6 (trichloromethyl)pyridine, dicyandiamide and 3,4-dimethylpyrazole-phosphate. Such inhibitors act to reduce nitrate leaching and nitrogen oxide emissions. Plant growth is increased. However, the effects can be variable and depend on timing of application, amount of nitrogen fertiliser applied and physical factors such as soil temperature, moisture, and pH.

Urease inhibitors have also been used to prevent loss of nitrogen to the atmosphere by volatilisation as ammonia. Urease inhibitors act by slowing the rate of hydrolysis. Other ways of reducing nitrogen loss are through farm management practices, including timing of application of fertiliser, split fertiliser applications, grazing management, pasture species choices, cropping type and landscape modification.

However, there remains a need for new products and methods for improving plant growth responses and development, while reducing nitrogen input.

SUMMARY

Embodiments described herein encompass a microbial bio-stimulant composition that has been shown to increase pasture productivity alone and in conjunction with the use of solid nitrogen fertiliser. The mode of action includes stimulating nitrogen uptake and amino acid synthesis.

It is an object of embodiments described herein to provide a means for stimulating plant growth with up to 50% less urea, or at least provides a useful alternative to other means of stimulating plant growth.

In one aspect, a method of improving plant growth by application of a bio-stimulant composition either combined or uncombined with urea and/or other agricultural compounds is provided. The method may also be used to reduce nitrogen input and improve plant development. The agricultural compounds may be urea, fertilisers, foliar fertilisers, herbicides, insecticides, fungicides, or mineral solutions.

In another aspect, a bio-stimulant composition for improving plant growth either combined or uncombined with urea and/or other agricultural compounds is provided. The composition may also be used to reduce nitrogen input and improve plant development. The agricultural compound may be urea, fertiliser, herbicide, insecticides, fungicides or foliar fertilisers or mineral solutions.

In a particular aspect, the bio-stimulant composition comprises a fermentation broth comprising one or more species or strains of microorganisms which have been grown in the fermentation broth and then killed or lysed to produce a mixture of cellular components in the fermentation broth (e.g., lysed fermentation broth).

In a further aspect, a method for combining the bio-stimulant composition described herein with urea and/or other agricultural compounds is provided. In one particular aspect, the method comprises dissolving urea in water and adding the bio-stimulant composition to the solution. This can be applied to the plants to achieve more even application (e.g., via spraying) than is possible with granular application of urea. This can also take advantage of the increases foliar uptake and decreased foliage nitrate levels of the bio-stimulant composition.

In a still further aspect, a formulation combining the bio-stimulant composition described herein with urea and/or other agricultural compounds is provided. The formulation can comprise dissolved urea added to the bio-stimulant composition. This formulation can be adapted, for example, for foliar applications (e.g., foliar sprays or drips). The formulation can be used to improve plant growth.

BRIEF DESCRIPTION OF THE DRAWINGS

Embodiments are described with reference to specific embodiments thereof and with reference to the figures.

FIG. 1: Field testing results for the bio-stimulant composition (Donaghys LessN® 40) compared to sprays containing the same amount of urea (U 40) and double the amount of urea (U 80) at Day 23.

DETAILED DESCRIPTION

The bio-stimulant is produced by fermentation of a single species or combination of microorganisms including but not limited to lactic acid bacteria and yeasts that are then killed or lysed. Any microorganism or combinations of microorganisms capable of fermentation can be used in accordance with the embodiments described herein. The fermentation can involve growing a liquid broth that includes carbohydrate and mineral sources for the microorganisms. Any fermentation media can be used, and many suitable media are well known in the art.

Bacteria useful for the embodiments described herein include but are not limited to *Lactobacillus plantarum, Streptococcus thermophilus* (also called *Streptococcus salivairus*) and *Propionibacter freudenreichii*. Embodiments encompass various species of *Lactobaccilius, Streptococcus*, and *Propionibacter*. As further examples, the invention encompasses *Lactobacillus acidophilus, Lactobacillus buchneri, Lactobacillus johnsonii, Lactobacillus murinus, Lactobacillus paraplantarum, Lactobacillus pentosus, Lactobacillus delbrueckii, Lactococcus lactis, Leuconostoc oenos, Bifidobacter bifidus, Propionibacter shermani, Propionibacter pelophilus*, and *Propionivibro limicola*.

Yeasts useful for the embodiments described herein include but are not limited to *Saccharomyces cerevisiae*. The embodiments encompass various species of *Saccharomyces*. As further examples, the embodiments encompass *Saccharomyces pastorianus, Saccharomyces boulardii, Saccharomyces bayanus, Saccharomyces exiguous, Saccharomyces pombe*, as well as species of *Candida, Pichia, Hanseniaspora, Metschnikowia, Issatchenkia, Kluyveromyces*, and *Kloeckera*.

In accordance with embodiments described herein, the microorganisms produce a range of growth promoting compounds including cytokinins, betaines, gibberellins and antioxidants. There is also a range of amino acids, oligopeptides and cell fragments resulting from the lysis of the microorganisms. In particular aspects, the microorganisms can be grown in the media to concentrations of about $10^4$ cfu/ml, about $10^5$ cfu/ml, about $10^6$ cfu/ml, about $10^7$ cfu/ml, about $10^8$ cfu/ml, about $10^9$ cfu/ml, about $10^{10}$ cfu/ml, about $10^{11}$ cfu/ml, about $10^{12}$ cfu/ml, about $10^{13}$ cfu/ml, about $10^{14}$ cfu/ml, or in a range of about $10^6$ to about $10^{10}$ cfu/ml, or about $10^7$ cfu/ml to about $10^9$ cfu/ml.

The microorganisms can be killed or lysed by various means, for example, by freezing, heating, bead beating, detergents including non-ionic and zwitterionic detergents, low pH treatment including by hydrochloric, hydrofluoric and sulphuric acids, and high pH treatment including by sodium hydroxide. Also included is enzymatic lysis including but not limited to one or more of types of cellulase, glycanase, lysozyme, lysostaphin, mannase, mutanolysin, protease and zymolase enzymes.

Included also is solvent treatment such as with sodium dodecyl sulfate treatment followed by acetone solvent use, or ultrasonic treatment. Further included are means which increase pressure followed by a rapid decrease in pressure such as is achievable with a pressure bomb, cell bomb, or with processors that provide high shear pressure such as valve type processors including but not limited to French pressure cell press or rotor-stator processors or fixed geometry fluid processors.

The compositions and formulations described herein can be applied to plants by various means, including sprays, sprinklers, drips, dips, drenches, dressings, oils, and any type of irrigation system. As non-limiting examples, embodiments encompass foliar sprays, turf sprays, in-furrow sprays, root dips, root drenches, stem drenches, seedling drenches, tuber drenches, fruit drenches, soil drenches, soil drips, and soil injections. As further examples, the compositions and formulations can be applied in dry form, e.g., granules, microgranules, powders, pellets, sticks, flakes, crystals, and crumbles.

For formulations, the bio-stimulant composition can be combined with urea, e.g., for concentrations of urea at about 0.1 kg/L, about 0.12 kg/L, about 0.15 kg/L, about 0.18 kg/L, about 0.2 kg/L, about 0.22 kg/L, about 0.25 kg/L, about 0.28 kg/L, about 0.3 kg/L, about 0.35 kg/L, about 0.38 kg/L, about 0.4 kg/L, about 0.42 kg/L, about 0.45 kg/L, about 0.48 kg/L, or about 0.50 kg/L, or in a range of about 0.15 kg/L to about 0.25 kg/L, or about 0.18 kg/L to about 0.22 kg/L, or about 0.35 kg/L to about 0.45 kg/L, or about 0.38 kg/L to about 0.42 kg/L.

The composition described herein can be used to stimulate plant growth and the plant immune system. It can be used to overcome periods of plant stress. In particular, the bio-stimulant composition described herein can be used to assist the plant to achieve more efficient nutrient utilisation. The composition described herein is understood to act as a biological growth promoter that assists pasture production through the stimulation of plant photosynthesis, proliferation of the fine feeder roots and subsequent increased nutrient uptake.

The bio-stimulant composition can be applied at a time when soil temperatures are conducive to pasture or crop growth response. The composition can be applied by diluting by a factor of at least one in ten and can be distributed by spraying or through irrigation. The bio-stimulant composition can be used for improving pasture growth and is also useful on a wide range of crops.

The composition described herein may comprise a range of naturally produced and balanced growth promotion factors. The principal precursors are forms of cytokinin (a microbial and plant hormone responsible for promoting cell division and growth), betaines (substances used by plant cells for protection against osmotic stress, drought, high salinity or high temperature) and oligopeptides (short chains of amino acids that improve nutrient uptake through cell membranes). Although plants produce their own cytokinin, production may be restricted when the plant is under stress.

The use of the composition described herein enhances nitrogen utilisation. It has also been shown to encourage white clover growth relative to perennial ryegrass. This has benefits because of the high feed value of white clover and the importance of root nodules of this plant in fixing atmospheric nitrogen so that more nitrogen is available for use by the plant itself and other pasture plants. In addition, the use of the composition described herein reduces the amount of urea that needs to be applied. This benefits the clover component of pasture because higher rates of nitrogen can potentially reduce nitrogen fixation rates of clover and also favours grass growth over clover growth.

EXAMPLES

The examples described herein are for purposes of illustrating embodiments described herein. Other embodiments, methods, and types of analyses are within the scope of persons of ordinary skill in the molecular diagnostic arts and need not be described in detail hereon. Other embodiments within the scope of the art are considered to be part of the embodiments described herein.

Example 1

Fermentation Broth

The bacteria *Lactobacillus plantarum, Streptococcus thermophilus* and *Propionibacter freudenreichii* and the yeast *Saccharomyces cerevisiae* were isolated and maintained using standard methods known in the art. A broth medium was prepared using Diffco™ Lactobacilli MRS Broth augmented with the following ingredients.

TABLE 1

| Fermentation broth composition (all ingredients per litre of broth) | |
|---|---|
| DiffcoTM Lactobacilli MRS Broth | 55 g |
| Urea | 2 g |
| Carrot Juice | 1.25 mL |
| Molasses powder from sugar cane | 2.5 g |

The broth was prepared by constant stirring while bring to the boil and keeping there for one minute. This ensured full dissolving of the broth medium, urea and molasses.

The broth was then sterilised in autoclave (121° C. for 15 mins) and poured into a sterilised 20 L bioreactor. After the broth was cooled to about 35° C., pure cultures of the three bacterial species (minimum of $10^6$ colony forming units or cfu s for each species) and one yeast species (minimum $10^4$ cfu's) were then added to the broth using standard sterile technique known in the art to avoid contamination with other microbial species. The fermentation was run for 12 days at 35° C. by which stage there were at least $10^8$ cfu per mL of the dominant species *Lactobacillus plantarum*.

The fermentation broth was then placed in a fixed geometry fluid processor for cell lysis of the microorganisms. Two passes were required with the broth being cooled in between passes to compensate for the temperature increase due to pressurisation and release. The process was optimised for pressure to a maximum of 200 MPa.

Example 2

Preparation of the Formulation with Dissolved Urea

Urea fertiliser prills were dissolved in water at a concentration of 40 kg urea per 197 L total volume. Dissolution was aided by agitation of the water without a requirement for heating the water.

The dissolving of urea is an endothermic process and the time taken to dissolve depends on the concentration of urea and total volume involved as well as the initial temperature of the water and the method of agitation. With constant stirring and an initial water temperature of 12° C., the complete dissolution of urea (sourced from Ballance Agri-nutrients Limited, Tauranga New Zealand) at the above concentration and volume took 7 minutes. Source and amount of hardener added to urea prills in their manufacture are likely to affect the speed of dissolution in water.

The dissolved urea solution had a pH of around 9.0. The majority of the nitrogen, however, was found to remain in the organic form. Titrametric determination as known in the art revealed only 0.004% ammonium nitrogen and 0.002% nitrate nitrogen expressed in terms of grams of these forms per 100 mL of solution.

Once the urea was fully dissolved, lysed fermentation broth as prepared in Example 1 was added at a rate of 3 L broth to 197 L volume of urea solution. As the broth had an acidic pH of 3.6 due largely to the presence of organic acid fermentation products, the pH of the total solution was brought closer to neutral to a pH of around 6.2. Both the dissolved urea and the comparatively small amount of broth had a low buffering effect on solution pH.

The prepared solution was then ready to be applied to pasture or suitable crops.

Example 3

Field Experiment Utilising the Formulation on Pasture in Conjunction with Dissolved Urea Fertiliser Introduction: The field trial's objective was to identify if Donaghys LessN® (3 L/ha) applied in combination with 40 kg/ha urea (18 kg N), would increase the pasture dry matter (DM) response to a level equivalent to 80 kg/ha urea (37 kg N/ha). Pasture DM accumulation was measured by Grass Master (GM) probe on Day one (pre-treatment, start point) and 21 Days after treatment application. The GM Probe estimated DM accumulation using pre-programmed calibration equation provided by the manufacturer.

Methodology: A dairy farm property with irrigation was selected in mid-Canterbury region of New Zealand in December 2007. A recently grazed paddock with even pasture cover was selected to reduce variability between plots. The paddock was in re-growth phase having just been grazed by stock. Livestock were excluded from the trial area during the trial period.

A complete randomised block design (CRBD) consisting of 4 treatments (FIG. 1) with 5 replicate plots used for each treatment. This provided a total of 20 plots, which was divided into 5 blocks. Within each block one replicate of all 5 treatments was randomly assigned.

Within each block, treatments were randomly allocated to plots, using a random number generator. Plots were 4 m wide by a 100 m long. The spray boom was 4 m wide. Plots were marked with 60 cm long flags, at 0, halfway and full length.

Pre-treatment pasture dry matter was estimated for each plot by using the Grass Master Probe. Measurements were taken on every other pace one way up the plot length, randomly dropping probe to near where foot falls but at least 15 cm away from body to avoid false reading. This resulted in around 50-65 readings for each plot. Individual readings were spoken into an audio recorder and later listened and entered into Excel sheet for analysis. Readings were taken in each plot without knowledge of what the plot treatment is to eliminate risk of bias. The probe was set to "slow" reading (i.e. takes around 3 seconds to read). The probe was left stable for each reading until it emitted a beep. Average pasture cover recorded on the first day was used as the baseline for each plot from which growth was based.

The spray tank was cleaned and the nozzles checked. The spray pump is set at 30 psi. The spray rig was calibrated, using containers to collect volume of spray over time information from each nozzle, to deliver 200 L per hectare equivalent using the amount of time to deliver given volume of water and maintaining an appropriate speed (10 km/hour).

Control: Fifty 50 liters of water was added to the spray tank. The pump was started 1-2 m prior to plot perimeter and the vehicle was driven steadily at the determined speed (around 10 km/hour) over each control plot. The tank was then emptied.

U40-(Dissolved Urea sprayed at 40 kg urea/ha): Twenty liters of water was added to the spray tank and then 10 kg or urea prills was added. The water was stirred until all urea dissolved. The tank was then topped up with approximately 23 L of water to make a total volume of 50L. The nozzles where checked again for correct operating and the pressure set at 30 psi. The pump was started 1-2 m prior to plot perimeter and the vehicle was driven steadily at the determined speed (around 10 km.hour) over each U40 plot. The tank was then emptied and rinsed with water.

Donaghys LessN® 40-(Dissolved Urea sprayed at 40 kg urea/ha with 3 L of the broth called Donaghys LessN®: Twenty liters of water was added to the spray tank and then 10 kg of urea prills was added. The water was stirred until all urea dissolved. Fermentation broth was at 0.75 L to the solution and then the tank was topped up with approximately 22.25 L of water to make a total volume of 50 L. The nozzles where checked again for correct operating and the pressure set at 30 psi. The pump was started 1-2 m prior to plot perimeter and the vehicle was driven steadily at the determined speed (around 10 km.hour) over each Donaghys LessN® 40 plot. The tank was then emptied and rinsed with water.

U80-(Dissolved Urea sprayed at 80 kg urea/ha): Thirty five liters of water was added to the spray tank and then 20 kg or urea prills was added. The water was stirred until all urea dissolved which took about 25 minutes. The tank was then topped up with approximately one liter of water to make a total volume of 50 L. The nozzles where checked again for correct operating and the pressure set at 30 psi. The pump was started 1-2 m prior to plot perimeter and the vehicle was driven steadily at the determined speed (around 10 km.hour) over each U80 plot. The tank was then emptied and rinsed with water.

Post Treatment-Pasture DM Measurements: Post-treatment pasture dry matter was assessed 23 days after treatment by using a Grass Master Probe using the methods described for pre-treatment readings.

Statistical Analysis: Data analysis was performed in Genstat using analysis of variance (ANOVA) in CRBD. The level of significance of treatment differences was assessed.

Results: Pasture growth was calculated from subtracting the relevant baseline pasture dry matter measurement from the pasture dry matter measurement at the end of each of the three grazing rotations. Donaghys LessN® 40 performed similarly to Urea 80 and both these treatments caused statistically significantly greater pasture growth than Urea 40 (which was not statistically significantly better than Control).

TABLE 2

Pasture dry matter production (kg/ha)

| Treatment | DM Rotation 1* |
|---|---|
| Control | 1322$^a$ |
| Urea 40 | 1527$^a$ |
| Urea 80 | 1979$^b$ |
| Donaghys LessN ® 40 | 1809$^b$ |

$^{a,b}$Numbers with a different letter beside them are statistically significantly different from each other (p < 0.05)

All publications and patents mentioned in the above specification are herein incorporated by reference. Any discussion of the publications and patents throughout the specification should in no way be considered as an admission that such constitute prior art, or widely known or common general knowledge in the field.

Where the foregoing description reference has been made to integers having known equivalents thereof, those equivalents are herein incorporated as if individually set forth. Although the invention has been described in connection with specific preferred embodiments, it should be understood that the invention as claimed should not be unduly limited to such specific embodiments. It is appreciated that further modifications may be made to the invention as described herein without departing from the scope of the invention. The invention illustratively described herein may be practiced in the absence of any element or elements, or limitation or limitations, which are not specifically disclosed herein as essential.

In addition, in each instance herein, in embodiments or examples of the present invention, the terms 'comprising', 'including', etc. are to be read expansively without limitation. Thus, unless the context clearly requires otherwise, throughout the description and the claims, the words 'comprise', 'comprising' and the like are to be construed in an inclusive sense as opposed to an exclusive or exhaustive sense; that is to say in the sense of "including but not limited to".

The invention claimed is:

1. A method effective in increasing pasture dry matter response comprising:
    applying to pasture a composition comprising:
        a fermentation broth formulated for foliar application, wherein the fermentation broth comprises a mixture of cellular components from one or more strains of bacteria and one or more strains of yeast which have been grown in a broth to a range of about $10^6$ to about $10^{10}$ cfu/ml and then lysed in the broth.

2. The method of claim 1, wherein the composition further comprises urea.

3. The method of claim 1, wherein the bacteria are selected from the group consisting of *Lactobacillus, Streptococcus*, and *Propionibacter* strains.

4. The method of claim 1, wherein the yeast are selected from the group consisting of *Saccharomyces, Candida, Pichia, Hanseniaspora, Metschnikowia, Issatchenkia*, and *Kloeckera* strains.

5. A method effective in stimulating nitrogen uptake in plants comprising:
    applying to a plant a composition comprising:
        a fermentation broth formulated for foliar application, wherein the fermentation broth comprises a mixture of cellular components from one or more strains of bacteria and one or more strains of yeast which have been grown in a broth to a range of about $10^6$ to about $10^{10}$ cfu/ml and then lysed in the broth.

6. The method of claim 5, wherein the plant is selected from the group consisting of corn, potato, and cotton.

7. The method of claim 5, wherein the bacteria are selected from the group consisting of *Lactobacillus, Streptococcus*, and *Propionibacter* strains.

8. The method of claim 5, wherein the yeast are selected from the group consisting of *Saccharomyces, Candida, Pichia, Hanseniaspora, Metschnikowia, Issatchenkia*, and *Kloeckera* strains.

9. A method effective in stimulating amino acid synthesis in plants comprising:
    applying to a plant a composition comprising:
        a fermentation broth formulated for foliar application, wherein the fermentation broth comprises a mixture of cellular components from one or more strains of bacteria and one or more strains of yeast which have been grown in a broth to a range of about $10^6$ to about $10^{10}$ cfu/ml and then lysed in the broth.

10. The method of claim 9, wherein the plant is selected from the group consisting of corn, potato, and cotton.

11. The method of claim 9, wherein the bacteria are selected from the group consisting of *Lactobacillus, Streptococcus*, and *Propionibacter* strains.

12. The method of claim 9, wherein the yeast are selected from the group consisting of *Saccharomyces, Candida, Pichia, Hanseniaspora, Metschnikowia, Issatchenkia*, and *Kloeckera* strains.

13. A method comprising:
    applying to pasture a composition comprising:
        a fermentation broth formulated for foliar application, wherein the fermentation broth comprises a mixture of cellular components from one or more strains of bacteria and one or more strains of yeast which have been grown in a broth to a range of about $10^6$ to about $10^{10}$ cfu/ml and then lysed in the broth.

14. The method of claim 13, wherein the bacteria are selected from the group consisting of *Lactobacillus, Streptococcus*, and *Propionibacter* strains.

15. The method of claim 13, wherein the yeast are selected from the group consisting of *Saccharomyces, Candida, Pichia, Hanseniaspora, Metschnikowia, Issatchenkia*, and *Kloeckera* strains.

16. The method of claim 13, wherein the pasture of clover.

17. The method of claim 13, wherein the composition further comprises urea.

18. The method of claim 16, wherein the clover is white clover.

\* \* \* \* \*